US007172762B1

(12) United States Patent
Roberts et al.

(10) Patent No.: US 7,172,762 B1
(45) Date of Patent: Feb. 6, 2007

(54) ERYSIPELOTHRIX RHUSIOPATHIAE ANTIGENS AND VACCINE COMPOSITIONS

(75) Inventors: David S. Roberts, Philadelphia, PA (US); Leroy A. Swearingin, Waterford, CT (US); Brian T. Suiter, Lincoln, NE (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/489,711

(22) Filed: Jan. 24, 2000

Related U.S. Application Data

(60) Provisional application No. 60/117,704, filed on Jan. 29, 1999.

(51) Int. Cl.
*A61K 39/02* (2006.01)
*A61K 39/00* (2006.01)
*A01N 63/00* (2006.01)

(52) U.S. Cl. .............. 424/234.1; 424/184.1; 424/825; 424/93.4; 530/825; 530/350

(58) Field of Classification Search ............ 424/234.1, 424/184.1, 93.1, 93.4, 825; 530/350, 825, 530/300, 806; 435/69.3
See application file for complete search history.

(56) References Cited

U.S. PATENT DOCUMENTS

| 3,962,421 | A | * | 6/1976 | Neurath ................... 424/89 |
| 4,709,017 | A | * | 11/1987 | Collier et al. ............. 530/350 |
| 5,069,901 | A | * | 12/1991 | Jones et al. .............. 424/199.1 |
| 5,695,769 | A | * | 12/1997 | Frantz et al. ............. 424/255.1 |
| 5,895,655 | A | * | 4/1999 | Eckhardt et al. .......... 424/240.1 |
| 6,013,264 | A | * | 1/2000 | Petre et al. ............... 424/227.1 |
| 6,111,089 | A | * | 8/2000 | Fukuda ..................... 536/23.5 |
| 6,156,337 | A | * | 12/2000 | Barenholz et al. ......... 424/450 |
| 6,277,379 | B1 | * | 8/2001 | Oaks et al. ............. 424/197.11 |
| 6,358,744 | B1 | * | 3/2002 | Volkin et al. ............... 436/8 |
| 6,372,225 | B1 | * | 4/2002 | Matsuda ................... 424/236.1 |
| 6,777,405 | B2 | * | 8/2004 | Barton et al. ............. 514/185 |
| 2006/0173060 | A1 | * | 8/2006 | Chang et al. .............. 514/389 |

FOREIGN PATENT DOCUMENTS

WO   WO 91/18627   * 12/1991

OTHER PUBLICATIONS

Wild RL. J. Am. Vet. Med. Assoc. 184: 944-949, 1984.*
Rappuoli R. Vaccine 12: 579-581, 1994.*
Zarkasie et al. J. Vet. Med. Sci. 58: 87-89, 1996.*
Sato, H., et al., Protective Activity and Antigenic Analysis of Fractions of Culture Filtrates of *Erysipelothrix rhusiopathiae*, Veterinary Microbiology, vol. 43, No. 2-3, 1995, pp. 173-182.
Timoney J. F. And Groschup M. M., Properties of a Protective Protein Antigen of *Erysipelothrix rhusiopathiae*, Veterinary Microbiology, vol. 37, No. 3-4, 1993, pp. 381-387.
Kobayashi, S. et al., Immunological Characterization of Protective Antigens Prepared by Alkaline Treatment of Whole Cells and From the Culture Filtrate of *Erysipelothrix*, Veterinary Microbiology, vol. 30, 1992, pp. 73-85.
Chemical Abstract Service of Takagi, H., et al., Recombinant Preparation of Protective Peptide Antigen and Use as Vaccine Against *Erysipelothrix rhusiopathiae*, Database Accession No. 133:149129.
Groschup, M. H., et al., Characterization of a Protective Protein Antigen of *Erysipelothrix rhusiopathiae*, Epidemiol. Infect., 107, 1991, pp. 637-649.
Sawada, T. And Takahashi, T., Cross Protection of Mice and Swine Inoculated with Culture Filtrate of Attenuated *Ersipelothrix rhusiopathiae* and Challenge Exposed to Strains of Various Serovars, Am J. Vet Res, vol. 48, No. 2, Feb. 1987, pp. 239-242.
McCutcheon's, Emulsifiers & Detergents, North American Edition, 1987 (McCutcheon Division, MC Publishing Co., Glen Rock, NJ).

* cited by examiner

*Primary Examiner*—S. Devi
(74) *Attorney, Agent, or Firm*—Timothy J. Gumbleton

(57) ABSTRACT

The invention relates to stabilized antigen compositions of *Erysipelothrix rhusiopathiae* and vaccine formulations containing such antigen compositions. Antigens of the invention are effective in providing long-term protection against erysipelas in animals.

4 Claims, No Drawings

ERYSIPELOTHRIX RHUSIOPATHIAE ANTIGENS AND VACCINE COMPOSITIONS

This application claims the benefit of U.S. Provisional Application No. 60/117,704, filed Jan. 29, 1999.

FIELD OF THE INVENTION

The invention relates to antigen compositions and vaccine formulations to prevent or control *Erysipelothrix rhusiopathiae* infection (Erysipelas) and methods of making and using those antigen compositions and vaccine formulations.

BACKGROUND OF THE INVENTION

Erysipelas has a worldwide distribution and is of economic importance throughout Europe, Asia, Australia and North and South America. Pigs 3 months through 3 years of age are most susceptible to erysipelas. Affected pigs often have swollen and stiff joints and they do not gain weight efficiently. Also, their carcasses are often trimmed or condemned by inspectors at packing houses.

About 10 years ago it was shown that the conventional practice of making *E. rhusiopathiae* vaccines from whole killed cultures was unnecessary. A bacterium-free filtrate worked just as well in protecting both pigs and mice against virulent challenge. Subsequent published research by Japanese and U.S. scientists has confirmed this finding and shown that *E. rhusiopathiae* releases into the culture medium an antigen that is a universal immunogen in that it immunizes pigs against all *E. rhusiopathiae* strains (Sawada and Takahashi, 1987, Am. J. Vet. Res. 48:239–242; Groschup et al., 1991, Epidemiol. Infect. 107:637–649). Groschup et al. showed that a 64 to 66 kDa protein in the culture protected mice against challenge with virulent *E. rhusiopathiae*. Having shown that such a protein also protects pigs, the USDA provides vaccine makers with a monoclonal antibody (mAb) to this protein for use in assaying the protein.

Although an effective vaccine to prevent erysipelas in pigs is very desirable, none of the many traditional erysipelas vaccines provides acceptable protection for weaned pigs. The problem is lack of duration of immunity. The pig industry requires a vaccine that, given at weaning, will protect pigs against this lethal, devastating disease until slaughter age, i.e., approximately 6 months. The USDA has specified this requirement as a standard for the licensing of new vaccines.

SUMMARY OF THE INVENTION

The invention relates to an antigen composition of *E. rhusiopathiae* and methods of making such an antigen composition. The invention also relates to a vaccine formulation that contains an antigen composition of *E. rhusiopathiae* and an adjuvant. The invention further relates to a method of using an antigen composition of the invention to vaccinate an animal, preferably a mammal or a bird. In particular, the invention relates to a method of vaccinating a pig, a lamb, a dog, a horse, a cow or a human with an antigen of the invention.

In one embodiment, stabilized antigens from the fluid fraction of *E. rhusiopathiae* cultures are described. In one aspect, a stabilizing agent is added to a supernatant or filtrate of an *E. rhusiopathiae* culture, preferably a concentrated supernatant or filtrate. A stabilizing agent is an agent capable of adsorbing the antigen. Non-limiting examples of stabilizing agents are aluminum hydroxide gel, aluminum phosphate gel, calcium phosphate gel, a zinc hydroxide/calcium hydroxide gel and an alum. In a preferred aspect, aluminum hydroxide gel is added to a concentrated supernatant such that the final concentration of the aluminum hydroxide gel is from about 10% v/v (i.e., 10% volume per volume concentration obtained by, e.g., mixing 9 volumes of the supernatant with 1 volume of the aluminum hydroxide gel) to about 40% v/v, more preferably about 30% v/v.

In another aspect, the antigen comprising the concentrated *E. rhusiopathiae* culture supernatant or filtrate and the stabilizing agent is diluted from about 10-fold to about 30-fold, preferably about 20-fold, when the antigen is formulated for use in a vaccine composition, thus bringing the concentration of the stabilizing agent in the vaccine composition down to less than about 5% v/v.

In another embodiment, *E. rhusiopathiae* is cultured and processed to obtain a supernatant or filtrate comprising an *E. rhusiopathiae* antigen. In one aspect, the *E. rhusiopathiae* culture is inactivated, for example, by adding formalin or beta propiolactone. In a further aspect, the *E. rhusiopathiae* culture broth is separated from the bacteria, for example, by centrifugation. In yet another aspect, the supernatant is concentrated about 10-fold, for example, by molecular filtration:

In another embodiment of the invention, a preservative is added to the antigen, for example, merthiolate, either with or without, ethylenediamine tetraacetic acid (EDTA). In a further embodiment of the invention, an antigen of the invention is combined with an adjuvant, for example, an adjuvant comprising a lecithin, an oil and one or more surfactants. In another embodiment of the invention, methods are described in which antigens and vaccines of the invention are used to vaccinate an animal.

DETAILED DESCRIPTION OF THE INVENTION

The invention relates to compositions and methods to prevent or control erysipelas. In one embodiment, the invention relates to antigens of *E. rhusiopathiae* and methods of making such antigens. The invention further relates to vaccine formulations that contain an antigen of the invention. The invention further relates to a method of using an antigen of *E. rhusiopathiae* to vaccinate an animal, preferably a mammal, or a bird. In a most preferred aspect, the mammal is selected from the group consisting of a pig, a lamb, a dog, a horse, a cow or a human.

The invention relates to antigens obtained from *E. rhusiopathiae* culture. Any strain of *E. rhusiopathiae* may be the source of antigens for the invention, for example strains described in U.S. Pat. No. 5,625,038. The culture from which the antigens may be isolated may be provided in a variety of ways. For example, the culture may be pure or substantially pure. More preferably, the antigens of the invention are obtained from a supernatant or filtrate of an *E. rhusiopathiae* culture. In a most preferred embodiment, antigens of the invention are obtained from the supernatant or filtrate of a pure or substantially pure liquid culture of *E. rhusiopathiae*.

*E. rhusiopathiae* may be cultured in a variety of ways as known in the art. See U.S. U.S. Pat. Nos. 5,625,038; 5,616,328; 5,417,971; 5,225,194; 4,981,685, which discuss the culturing of bacteria. For example, *E. rhusiopathiae* may be cultured as described in the illustrative examples provided below. *E. rhusiopathiae* may also be cultured as described in Sawada and Takahashi, 1987, Am. J. Vet. Res.

48:239–242 and in Groschup et al., 1991, Epidemiol. Infect. 107:637–649. General background on culturing and processing of prokaryotic cells is provided in Maniatis, et al., 1982, *Molecular Cloning, A Laboratory Manual*, Cold Spring Harbor Laboratory Press, Cold Spring Harbor, N.Y.; Ausubel, et al., 1989, *Current Protocols in Molecular Biology*, Greene publishing Associates and Wiley Interscience, NY; Sambrook et al., 1989, *Molecular Cloning, A Laboratory Manual*, 2d. ed., Cold Spring Harbor Laboratory Press, Cold Spring Harbor, N.Y., all of which are incorporated herein by reference in their entireties.

In a preferred embodiment, the culture is inactivated by adding formalin (about 0.5% v/v final concentration). In another preferred embodiment, antigens of the invention are obtained from the supernatant or filtrate of an *E. rhusiopathiae* culture. A culture supernatant or filtrate, in a preferred embodiment, is concentrated about 10-fold and aluminum hydroxide gel (preferably REHYDRAGEL™) is added to the concentrated supernatant or filtrate at a final concentration of about 30% v/v to stabilize the antigen. In another preferred embodiment, a vaccine composition is formulated comprising the antigen and an adjuvant with the adjuvant comprising, for example, about 25% v/v of the vaccine composition. In another preferred embodiment, thimerosal (about 0.01% v/v final concentration) with EDTA (about 0.07% v/v final concentration) are added to the antigens as preservative. A preferred adjuvant, herein referred to as "No.1 Adjuvant", comprises about 2% v/v lecithin, about 18% v/v mineral oil, and about 8% v/v surfactant (e.g., about 5.6% v/v TWEEN 80™, polyoxyethylene sorbitan monooleate, and about 2.4% v/v SPAN 80™, sorbitan monooleate), with the remaining volume being a saline solution (e.g., Dulbecco PBS). This adjuvant is described in U.S. Patent Application Ser. No. 60/117,705, filed Jan. 29, 1999, entitled "Adjuvants for Use in Vaccines", which is incorporated herein by reference.

Antigens of the invention are obtained from *E. rhusiopathiae* which may be provided in ways known in the art, for example in liquid culture. In a preferred embodiment of the invention, an *E. rhusiopathiae* culture from which an antigen is isolated is inactivated prior to using the antigen in a vaccine formulation. In a most preferred embodiment, the *E. rhusiopathiae* culture is inactivated prior to separating the liquid fraction from the bacteria. The inactivation of the *E. rhusiopathiae* culture is carried out for a variety of purposes, for example to kill the bacteria or to inactivate proteases or to preserve the antigen.

A culture containing antigens of the invention may be inactivated in a variety of ways known in the art. For example, the culture may be exposed to an inactivating agent, i.e., an agent capable of killing *E. rhusiopathiae*. An inactivating agent useful in the practice of the invention permits the antigen of the invention to elicit an immune response in an animal to protect said animal from erysipelas. Inactivating agents known in the art can be used, for example, formalin (formaldehyde), beta propiolactone or other chemical agents having properties similar to these agents. Suitable chemical agents for inactivation of bacteria can be determined by one of ordinary skill in the art, for example by contacting bacteria with a particular chemical, and determining if the bacteria are killed and the antigens therewith still active in their ability to produce protective antibody by, for example, vaccinating mice with the treated bacteria. Also, see U.S. Pat. No. 5,225,194, which discusses the inactivation of bacteria.

Separation and Concentration of *E. rhusiopathiae* Culture Fluid

In a preferred embodiment, antigens of the invention are obtained from the fluid fraction of an *E. rhusiopathiae* culture. *E. rhusiopathiae* may be cultured and the bacteria separated from the culture broth, for example by centrifuging or filtering a liquid culture. A culture of *E. rhusiopathiae* useful for the isolation of an antigen of the invention may be provided in any way known in the art. For example, the *E. rhusiopathiae* may be grown in a broth or medium so that the bacteria multiply rapidly, i.e., log phase. In a preferred embodiment, the culture used to prepare an antigen of the invention is in log phase, more preferably in late log phase, at the time when the processing of the culture is initiated.

In a preferred embodiment, *E. rhusiopathiae* culture is processed to separate all or substantially all bacteria from the broth or medium in which they were grown. For example, about 90% of the bacteria may be removed from the broth or medium, more preferably about 95% of the bacteria are removed, more preferably at least about 98% of the bacteria are removed. *E. rhusiopathiae* may be separated from the culture broth or medium in any way known in the art. For example, *E. rhusiopathiae* culture may be centrifuged to separate the bacteria from the broth or medium. Any centrifuge known in the art that is capable of sedimenting *E. rhusiopathiae* bacteria is suitable to separate the cells from the broth or medium. For example, a continuous-flow centrifuge may be used. Background on how to remove bacteria from a culture medium is provided in Maniatis, et al., 1982, *Molecular Cloning, A Laboratory Manual*, Cold Spring Harbor Laboratory Press, Cold Spring Harbor, N.Y.; Ausubel, et al., 1989, *Current Protocols in Molecular Biology*, Greene publishing Associates and Wiley Interscience, NY; Sambrook et al., 1989, *Molecular Cloning, A Laboratory Manual*, 2d. ed., Cold Spring Harbor Laboratory Press, Cold Spring Harbor, N.Y.

In another aspect, *E. rhusiopathiae* may be removed from the culture medium or broth by filtration through a filter that retains the bacteria but does not retain the antigen of the invention. Many filters suitable to separate the bacteria from the antigen in the broth or medium are known in the art. For example, a filter useful to separate the bacteria from the fluid fraction has a mean pore diameter of from about 0.1 microns to about 0.5 microns, more preferably about 0.2 micron.

The fluid fraction obtained from a culture of *E. rhusiopathiae* ("fluid fraction") as described above may be concentrated. In one embodiment, the fluid fraction may be concentrated about 3-fold to about 30-fold, for example, about 3-fold, or about 6-fold, or about 10-fold, or about 15-fold, or about 20-fold, or about 30-fold. The fluid fraction may be concentrated in any way known in the art. In a preferred embodiment, the fluid fraction may be concentrated using hollow fiber filtration. In one aspect, hollow fiber filtration is carried out with a molecular weight cut-off of from about 5,000 kilodalton to about 50,000 kilodalton, more preferably from about 10,000 kilodalton to about 30,000 kilodalton. See also U.S. Pat. No. 5,225,194, which discusses the concentration of a fluid fraction of a bacterial culture.

The fluid fraction also may be concentrated by freeze drying or lyophilization. In another aspect, the fluid fraction may be concentrated by precipitation of the proteins and polypeptides in the fluid fraction followed by resuspension of the precipitate. Proteins may be precipitated from the fluid fraction using any method known in the art, for example, through precipitation by polyethylene glycol, ethanol or ammonium sulfate. Following precipitation, the sediment may be resuspended in any solution suitable for the preparation of a vaccine formulation, for example, a saline solution.

Stabilization of *E. rhusiopathiae* Antigen

Antigens obtained from a fluid fraction of an *E. rhusiopathiae* culture are effective immunogens to prevent or control erysipelas in an animal. However, the lack of stability of those antigens following removal of the bacteria is a serious problem when using these antigens in a vaccine composition. The invention solves that problem and is based, in part, on the discovery that antigens in a fluid fraction of an *E. rhusiopathiae* culture can be stabilized by adding a stabilizing agent.

Any stabilizing agent known in the art may be used to stabilize the antigens of the invention. In a preferred embodiment, a stabilizing agent is capable of adsorbing an antigen of an *E. rhusiopathiae* culture fluid fraction. A suitable stabilizing agent can maintain the antigenic potential of a fluid fraction of an *E. rhusiopathiae* culture or otherwise slow the degradation of its antigenic potential after removal of the bacteria. Such stabilizing effect of an agent can be determined with experimentation. For example, one can incubate two samples of a fluid fraction of an inactivated *E. rhusiopathiae* culture at 37° C. for a period of time, for example from about 14 to about 28 days, one sample with and one without a chemical agent being tested for its use as a stabilizing agent. The samples are then tested in a vaccination of mice according to the standard mouse potency test (9 CFR 113.119(c)), using an adjuvant, for example No. 1 Adjuvant. A higher proportion of protected animals in the group given the vaccine treated with the chemical agent than in the group given the untreated vaccine or in the unvaccinated control animals indicates that the antigen in the chemically-treated vaccine has been stabilized.

The above-described experiment illustrates an accelerated stability test at a higher temperature (37° C.) than is normally used for storage. Normally, antigen preparations are stored in cold temperatures, for example from about 2° C. to about 8° C. 28 days stability at 37° C. indicates stability for a longer period of time in normal cold storage, i.e. for a period of several years. In one embodiment, the antigen is stabilized in cold temperatures for up to about 5 years according to the present invention, more specifically for up to about 3 years in cold temperatures. In another embodiment, the antigen is stabilized for at least one year in cold temperatures according to the present invention.

A variety of agents is known in the art that are capable of adsorbing an antigen, for example, an aluminum hydroxide gel, an aluminum phosphate gel, a calcium phosphate gel, a zinc hydroxide/calcium hydroxide gel and an alum (e.g., a potash alum) are useful as stabilizing agents. In a preferred embodiment, aluminum hydroxide gel, for example, REHYDRAGEL™ is used as a stabilizing agent. (See U.S. Pat. Nos. 5,616,328 and 5,232,690, which discuss metal gels and their uses.)

In one embodiment, a metal hydroxide gel, for example, aluminum hydroxide gel (e.g., REHYDRAGEL™) is added to a final concentration of from about 10% v/v to about 40% v/v, for example, about 10% v/v, or about 20% v/v, or about 30% v/v, or about 40% v/v in the antigen preparation. In a preferred embodiment, the aluminum hydroxide gel (e.g., REHYDRAGEL™) is added to a final concentration of about 30% v/v in the antigen preparation.

An antigen preparation containing the stabilizing agent may be used to formulate a vaccine composition, for example by adding an adjuvant and a diluent such as saline, so that the antigen preparation and the stabilizing agent are diluted. Such dilution may be helpful to avoid or substantially avoid undesired side effects of the vaccine formulation in the animal. For example, an antigen formulation containing a metal hydroxide gel, for example, aluminum hydroxide gel (e.g., REHYDRAGEL™), is diluted upon adding to a vaccine formulation by about 5-fold, or about 10-fold, or about 15-fold, or about 20-fold, or about 25-fold, or about 30-fold. In a preferred embodiment, an antigen formulation containing aluminum hydroxide gel (e.g., REHYDRAGEL™) at a final concentration of about 30% v/v is diluted through addition to the vaccine formulation by about 20-fold, giving a final aluminum hydroxide gel concentration of about 1.5%.

Vaccine Compositions Comprising Antigens of *E. rhusiopathiae*

An antigen of the invention may be used in a vaccine composition to immunize an animal. In one embodiment, the vaccine composition contains an antigen of the invention and an adjuvant. In a preferred embodiment, an adjuvant useful for a vaccine composition of the invention comprises a lecithin, an oil, and a surfactant. A vaccine composition formulated with a preferred adjuvant contains a lecithin at from about 0.25% to about 12.5% v/v, more preferably from about 0.5% to about 5%, and most preferably from about 0.5% to about 1.25% v/v, an oil at from about 1% to about 23% v/v, more preferably from about 3.5% to about 10% and most preferably about 4.5%, and an amphiphilic surfactant at from about 1.5% to about 6% v/v, more preferably from about 1.5% to about 4% and most preferably about 2% v/v. Preferably the adjuvant has 2 amphiphilic surfactants, for example TWEEN™ and SPAN™ surfactants, of which one predominantly in the aqueous phase (e.g., TWEEN 80™) of the vaccine composition and one in the oil phase (e.g., SPAN 80™). Preferably, when TWEEN 80™ and SPAN 80™ are used as surfactants, the concentration of TWEEN 80™ is about 1½ to about 3 times as high as the concentration of SPAN 80™, preferably about 2 times. A preferred adjuvant contains an aqueous carrier solution, for example, phosphate-buffered saline (PBS) (.g., Dulbecco PBS). A lecithin and an oil suitable for an adjuvant for the vaccine compositions is a mixture of lecithin in DRAKEOL™ 5 Lt Mineral Oil. Lecithin may be obtained from Central Soya, Fort Wayne, Ind. See also U.S. Pat. No. 5,084,269, which discusses adjuvant compositions. TWEEN™ and SPAN™ surfactants may be obtained from Van Waters and Rogers, Omaha, Nebr.

In another embodiment, adjuvants known in the art, for example, oil emulsions, aluminum hydroxide, muramyl dipeptides, zinc calcium hydroxide, pyridine, aluminum hydroxide, oils and saponins may be used in a vaccine formulation of the invention as described in U.S. Pat. Nos. 5,846,527; 5,417,971; 5,232,690, which discuss adjuvants.

A preferred vaccine composition is formulated with from about 10% to about 50% of its volume being an adjuvant composition, more preferably from about 15% to about 35%, more preferably from about 20% to 30% and most preferably about 25%.

A vaccine formulation may be administered to a subject per se or in the form of a pharmaceutical or therapeutic composition. Pharmaceutical compositions comprising the antigens may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

Systemic formulations include those designed for administration by injection, e.g. subcutaneous, intradermal, intramuscular or intraperitoneal injection.

For injection, the antigens may be formulated in aqueous solutions, preferably in physiologically compatible buffers such as Hanks's solution, Ringer's solution, phosphate buffered saline, or any other physiological saline buffer. The solution may contain formulatory agents such as suspending, stabilizing and/or dispersing agents. Alternatively, the proteins may be in powder form for constitution with a suitable vehicle, e.g., sterile pyrogen-free water, before use.

In addition to the formulations described previously, the antigens may also be formulated as a depot preparation. Such long acting formulations may be administered by implantation (for example subcutaneously or intramuscularly) or by intramuscular injection. Thus, for example, the antigens may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver an antigen. Certain organic solvents such as dimethylsulfoxide also may be employed, although usually at the cost of greater toxicity. Additionally, the antigens may be delivered using a sustained-release system, such as semipermeable matrices of solid polymers containing the therapeutic or vaccinating agent. Various sustained-release materials have been established and are well known by those skilled in the art. Sustained-release capsules may, depending on their chemical nature, release the antigens for a few weeks up to over 100 days. Depending on the chemical nature and the biological stability of the agent, additional strategies for antigen stabilization may be employed.

Determination of an effective amount of the antigen for administration is well within the capabilities of those skilled in the art, especially in light of the detailed disclosure provided herein.

An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the antigens of the invention may be administered in about 1 to about 3 doses over about a 2–36 week period. Booster vaccinations may be given periodically thereafter. Alternative protocols may be appropriate for individual animals. A suitable dose is an amount of antigen that, when administered as described above, is capable of raising an immune response in an immunized animal sufficient to protect the animal from E. rhusiopathiae infection for at least 4 to 12 months.

The amount of antigen in a dose is specified in terms of the optical density ($E_{625}$) of the culture at inactivation, as opacity units. If at inactivation, the optical density is 4.0, e.g., one ml of culture supernatant or filtrate, prepared from the culture, will contain four opacity units, 0.5 ml will contain 2 opacity units, etc., even though the source of opacity, the bacterial cells, has been removed. If a supernatant fluid containing, e.g., 5 opacity units per ml is concentrated 12 fold, by molecular filtration, the concentrated fluid will have a value of 60 opacity units per ml. In general, the amount of antigen in a dose of vaccine may range from about 1 to about 12 opacity units, preferably from about 2 to about 4 opacity units. Suitable dose volume will vary with the route of injection and the size of the host, typically from 0.1 to about 5 ml. Preferably, when the host is a pig the pig is at least two weeks old.

EXAMPLES

The vaccination study presented below demonstrated that a vaccine as described herein with No.1 Adjuvant when given to piglets in a 2-dose regimen at approximately 3 and 6 weeks of age, provided significant protection against virulent challenge at 20 weeks following a second vaccination. The antigen with No.1 Adjuvant also induced substantial antibody responses as shown by serum ELISA titers at two weeks following vaccination but, at time of challenge, these titers had waned and individual titers did not correlate closely with protection. The same antigen in saponin adjuvant and administered in the same way induced lower ELISA titers and proved inadequate in protecting pigs from virulent challenge at 20 weeks following a second vaccination.

The challenge model worked very well in that all 10 control pigs developed clinical signs of erysipelas following challenge (Table 2). Three pigs met the elevated temperature criterion and another five were *E. rhusiopathiae* culture-positive. The remaining two control pigs did not meet either of the above criteria; however, they were depressed for several days and had metastatic skin lesions characteristic of the disease and therefore were humanely killed. By contrast, in the group vaccinated with the vaccine containing No. 1 Adjuvant, 15 of the 20 pigs were completely protected (Table 3).

An experimental vaccine containing an antigen of *E. rhusiopathiae* of the invention with No.1 Adjuvant, when given to piglets in a 2-dose regimen at approximately 3 and 6 weeks of age, provided significant protection against development of clinical erysipelas from virulent challenge at 20 weeks following a second vaccination, see Table 3, infra. Furthermore, a similar experimental vaccine with saponin adjuvant, when given to piglets according to the same regimen, did not protect against development of clinical erysipelas from virulent challenge at 20 weeks following a second vaccination. Finally, a vaccination containing an antigen of the invention, regardless of adjuvant used, induced a substantial serological response that peaked at two weeks following second vaccination.

The invention having been described, the following examples are offered by way of illustration and not limitation.

Example 1

*E. rhusiopathiae* Culture

*E. rhusiopathiae* strain CN 3342 is cultured in medium containing Difco Proteose Peptone at a concentration of 2.75%, Difco Yeast Extract (0.55%), TWEEN 80™ (0.2%), $K_2HPO_4$ (0.217%) and $KH_2PO_4$ (0.061%) in deionized water. The pH of the medium is adjusted to 7.2 with 5N NaOH. The medium is steam sterilized at a minimum of 122° C. for 30 to 90 minutes. After autoclaving, sterile 50% dextrose solution is added to a final concentration of 3% w/v.

Working seed cultures are prepared by removing a cryotube of the master seed lot from frozen storage (minus 70° C.), rapidly thawing it, and aseptically transferring the contents to a flask of medium. The flask is incubated at 37° C. for 12 to 36 hours, with shaking, and checked for purity by Gram staining. When found to be pure, the culture was mixed with sterile glycerin (10%), dispensed into cryotubes in 1 mL amounts, and stored frozen.

Seed vessels containing production medium are inoculated with 0.01 to 2% of master or working seed. Seed fermenters, when used, containing 10 to 100 liters of production medium, are inoculated with 1 to 5% of culture from a seed flask. A production fermenter containing 200 to 10,000 liters of production medium is inoculated with 0.5 to 5% of culture from the seed fermenter.

Production cultures are incubated at a setpoint of 37±20° C. with stirring. Incubation times vary from 4 to 24 hours. Sterile 10N sodium hydroxide solution is added to the culture throughout the incubation period to maintain a pH of 7.2±0.1. During the growth phase, periodic additions of dextrose are made.

Prior to harvesting, the culture is examined microscopically for purity, cell morphology, and Gram reaction. Growth is monitored by measuring the optical density of the culture at 625 nm. Cultures are harvested when they have an optical density of 4.0 or higher at 625 nm.

Example 2

Preparation of E. rhusiopathiae Vaccine

A formalin solution was added to cultures to a final concentration of 0.5% (v/v) to inactivate the culture. The culture was transferred to a sterile tank and placed in a 37±2° C. incubator for a minimum of 24 hours (and a maximum of 60 hours) under constant stirring. Cultures not immediately processed were stored at 2 to 8° C. for up to 7 days. The inactivated culture was clarified by passage through a continuous-flow centrifuge. The fluid fraction was retained for further processing, and the bacteria were discarded.

In an experiment, 10× concentrates were made in a filtrate of E. rhusiopathiae cultures inactivated with either beta propiolactone ("BPL"), 0.1% v/v final concentration, or formalin, 0.2% v/v final concentration (at 37° C. for at least 24 hours). An enzyme-linked immunosorbent assay (ELISA) specific for the 64 to 66 kDa protein found in culture filtrate of E. rhusiopathiae (Groschup et al., 1991, Epidemiol. Infect. 107:637–649 and U.S. Pat. No. 5,625, 038) was carried out to determine the effect of inactivation and stabilization on the presence of the 64 to 66 kDa protein. Consistent with earlier findings that formalin inactivation of the culture decreased the ELISA assay value of the protein, the BPL concentrate had an assay value about 4 times that of the formalin concentrate. After incubation at 370° C., for 14 days, the BPL concentrate had lost about 80% of its value, compared to about 40% for the formalin concentrate. In both cases, however, the prior addition of REHYDRAGEL™, 30% v/v, as a stabilizing agent, see below, prevented most of the loss and virtually all of it in the case of the formalin preparation. A small study in pigs indicated that the fluid fraction of formalin-inactivated cultures was more effective than that of cultures inactivated with BPL in protecting pigs against challenge with virulent E. rhusiopathiae.

The fluids were concentrated, 6× to 20× (usually about 10×) by hollow fiber filtration (nominal molecular weight cut-off×10,000 kilodalton) following centrifugation. The fluids were stabilized following concentration by the addition of aluminum hydroxide gel.

In order to stabilize the immunogen, aluminum hydroxide gel was added slowly with stirring to the concentrated fluids to a final 30% (v/v)(30 volumes of gel to 70 volumes of concentrate). After 20 fold dilution of the concentrate in the vaccine the Al gel content was only about 1.5%, not enough to cause negative reactions at the injection site. A titration to determine the amount of Al gel required to adsorb all the protective protein in an E. rhusiopathiae culture fluid fraction concentrated tenfold, showed that more than 95% was adsorbed by 32% v/v REHYDRAGEL™ (Reheis, Berkeley Heights, N.J.). Thimerosal (i.e., MERTHIOLATE™) (Dimportex, Spain, imported through Flavine Inc., Klosters, N.J.) was added as preservative to the product in a final concentration of approximately 0.01% (w/v). The concentration of thimerosal was kept at about 0.01% w/v in the antigen composition and in a vaccine composition that contained the antigen of the invention. EDTA was added at a final concentration of approximately 0.07% (w/v) (Sigma, St. Louis, Mo.).

The adjuvant used was No.1 Adjuvant. 1000 mL of No.1 Adjuvant were made from 200 mL filter sterilized lecithin-oil solution (10% lecithin in DRAKEOL™ mineral oil), autoclaved TWEEN 80™ (56 mL) and SPAN 80™ (24 mL), and phosphate buffered saline (Dulbecco PPPBS) (720 mL). The lecithin-oil solution and SPAN 80™ were combined and mixed in a sterile tank for at least 1 hour at room temperature until emulsification was complete. The saline and TWEEN 80™ were combined and mixed in a sterile tank for at least 1 hour at room temperature. The oil mixture was emulsified with the aqueous mixture using a Ross emulsifier. Emulsification was continued by recirculation until all of the adjuvant was added into the saline. The emulsion was then passed twice through a Gaulin press at room temperature. The adjuvant was stored at 2 to 8° C.

5 L of vaccine were made by adding 1 L of adjuvant to 3 L of aqueous phase. The aqueous phase was comprised of sufficient stabilized concentrate to give a final antigen content of 3.2 opacity units per 2 ml dose of vaccine, plus sufficient saline to make up the volume to 5 L. Opacity units are defined as the optical density ($E_{625}$) at harvest multiplied by the concentration factor.

Example 3

E. rhusiopathiae Vaccination and Challenge of Pigs

The eighth subculture (MS+8) of E. rhusiopathiae, strain CN3342, was used to produce the vaccines. One dose level of stabilized, clarified E. rhusiopathiae antigen (3.2 opacity units ["OU"]) was used, as calculated from the optical density (OD) of the culture at inactivation. One OU was equivalent to 1 mL of fluid with an OD (determined at 625 nm) of one. No.1 Adjuvant or saponin (0.05% w/v, obtained from Berghausen Chemical Company, Cincinnati, Ohio) was used as adjuvant. Specifically, a culture of E. rhusiopathiae, strain CN3342, was grown to an OD of 5.28. The culture was inactivated for 24 hours with 0.5% formalin. Following inactivation, the bacteria were removed by centrifugation. The fluid fraction was then concentrated using an ultrafiltration unit with a nominal molecular weight cutoff of 10,000 kDa. The fluid fraction was concentrated approximately 13.4-fold. The antigen was stabilized by adding REHYDRAGEL™ (30% v/v) to the concentrated material. The adsorbed concentrate was stored at 4° C. until vaccine formulation. Vaccines were formulated with No.1 Adjuvant or 0.05% saponin as adjuvant. Stabilized antigen was diluted in saline (150 mM sodium chloride and 4 mM phosphate) to arrive at the final concentration. Ethylenediaminotetraacetate (EDTA, 0.07%) and thimerosal (0.01%) were added in the final vaccine formulations. Phosphate-buffered saline was used as placebo. Table 1 summarizes the treatment groups, vaccine treatments, and numbers of piglets vaccinated and challenged

TABLE 1

Vaccinated and challenged piglets by treatment (vaccine) group

| Treatment group | Antigen | Adjuvant | No. of piglets vaccinated | No. of piglets challenged |
|---|---|---|---|---|
| T01 | placebo | none | 16 | 10 |
| T02 | 3.2 OU | No. 1 Adjuvant | 26 | 20 |
| T03 | 3.2 OU | saponin | 16 | 10 |

A satisfactory challenge was evidenced in controls by a high body temperature (40.9° C. [105.6° F.] or higher on at least two consecutive days), by culture at necropsy, and/or by clinical signs characteristic of infection with $E.$ $rhusiopathiae$. Clinical signs considered characteristic of disease included sudden death, depression, hyperemia of the abdomen and ears, metastatic skin lesions, and stiffness or joint involvement. Pigs that had clinical signs but did not meet the temperature criterion were killed and blood, spleen, and liver were cultured in attempts to isolate $E.$ $rhusiopathiae$.

Fisher's exact test was used to determine if there was a difference in the percentage of animals protected with different vaccines ($P<0.05$). A priori contrasts were constructed to compare each dose group to controls and to compare each group to the average of all other dose groups. The relationships between type of vaccine given and serological responses of each group of piglets were done for the 2-month of age, 3-month of age, 4-month of age, 5-month of age, and prechallenge bleedings using logistic regression. The relationship between vaccine-induced titers at the time of challenge with disease status (protected/not protected) was assessed using logistic regression. The 5% level of significance was used to declare the relationship real.

Twenty pregnant sows/gilts, having low (#800) ELISA serological titers to $E.$ $rhusiopathiae$ were obtained from Riddell Farms, Albert City, Iowa and housed in isolation rooms at the University of Nebraska Department of Veterinary and Biological Sciences.

ELISA serological titers were determined in a whole cell direct antigen binding ELISA as follows. See U.S. Pat. No. 4,918,163, which describes the preparation of antigen coated plates and an ELISA using such plates. First, $E.$ $rhusiopathiae$ were grown as described in Example 1 and harvested from a log phase culture. The optical density at 640 nm was recorded and converted to cells/mL using a table established through counts of bacteria from solutions with different optical densities. The live bacteria were diluted in PBS (Dulbecco PBS, Sigma, St. Louis, Mo.) to a density of about $1.1 \times 10^9$ cells/mL. The live bacteria diluted in PBS were bound to plates for the ELISA. To prepare the plates, 100 µl of 0.1% v/v glutaraldehyde (Sigma, St. Louis, Mo.) in PBS were added into each well, the wells were covered and the plates were incubated at 37° C. for 1 hour. The glutaraldehyde in PBS was removed from each well and the wells were dried with absorbent towels. 100 µl of the live bacteria in PBS at a density of about $1.1 \times 10^9$ cells/mL were added to each well. The plates were centrifuged at 2000 rpm for 5 minutes at 22° C. Then, 200 µl of 1% polyvinyl alcohol (Aldrich, Milwaukee, Wis.) in PBS (PVA/PBS) were added to each well, the wells were covered and the plates were held overnight at 4° C. The contents of the wells of the plates was transferred to a bactericidal solution and the wells were washed with PBS. The wells were covered with gauze and dried at room temperature (about 1 hour).

The ELISA procedure was carried out as follows using the plates with bound bacterial whole cell antigen. First, the pig sera was diluted, including a positive control, in 1% PVA/PBS. All unknown sera were diluted at 1:50 and the positive control used at 1:200. 200 µl of each sample were added to a well in a row A column. 100 µl of 1% PVA/PBS were added in the remaining wells. 2-fold serial dilutions on each sample were run in rows B–H. The wells were covered and incubated 1 hour at 37° C. Then, the wells were washed 3 times with PBST. 100 µl of a 1:2000 dilution of goat anti-swine IgG (H & L) peroxidase conjugate (Kirkegaard and Perry, Gaithersburg, Md.) prepared in 1% PVA/PBS were added to each well. The wells were again covered and incubated 1 hour at 37° C. The wells were washed 3 times with PBST. 100 µl of ABTS substrate (2,2'-azino-di-(3ethylbenzthiazoline sulfonic acid) obtained from Kirkegaard and Perry, Gaithersburg, Md.) were added to each well and the plates were incubated at room temperature for 10 minutes. The plates were shaken for 10 seconds on a microplate shaker prior to reading the absorbance of each well at 405–490 nm using a plate reader blanked. The end point titer of each unknown serum was the dilution of the serum in which the absorbance was greater than the absorbance of a 1:3200 dilution of the positive control.

Sows were bled 0 to 10 days prior to farrowing to determine their $E.$ $rhusiopathiae$ antibody titers. Piglets were randomized based on sows* serological titers and farrowing dates. Fifty eight (58) piglets derived from these sows/gilts were bled and vaccinated at approximately 3 weeks of age with one of the two experimental $E.$ $rhusiopathiae$ vaccines or the placebo (groups listed in Table 1). At approximately 4 weeks of age the piglets were weaned. At approximately 6 weeks of age the piglets were bled and revaccinated with the same vaccine. At approximately 2 months, 3 months, 4 months and 5 months of age all pigs were bled. At approximately 5½ months of age, all spare pigs were removed from the study. At approximately 6 months of age (20 weeks after second vaccination) pigs were bled and 40 pigs were challenged intramuscularly with 2 mL of a virulent culture of $E.$ $rhusiopathiae$ (237 mouse $LD_{50}$, $1.74 \times 10^9$ colony-forming units/mL) grown from a culture provided by the National Veterinary Services Laboratory. Animals were monitored for signs of clinical disease and by rectal temperature for 2 days prior to challenge, the day of challenge, and the 7 days following challenge. Any control animal meeting the criterion for elevated rectal temperature (40.9° C.) was taken off study and treated with injectable penicillin. Any control animal that had clinical signs of disease, but did not meet the elevated rectal temperature criterion was humanely killed, necropsied, and samples of whole blood, spleen, and liver were cultured for $E.$ $rhusiopathaie$. Any control animal that died was necropsied and samples of spleen and liver were cultured for $E.$ $rhusiopathiae$. Any vaccinated animal meeting the criterion for elevated rectal temperature (40.9° C.) and/or clinical signs of disease was taken off study and treated with injectable penicillin. Any vaccinated animal dying following challenge was necropsied and samples of spleen and liver were cultured for *E. rhusiopathiae*. Antibody titers to *E. rhusiopathiae* were determined by ELISA described above and correlation of antibody titers with clinical protection was done.

ELISA titers were determined on the sera from the single blood sample obtained from the sows and all blood samples from the 7 sampling periods from the piglets. Aerobic bacterial cultures (48 hours, 37° C., blood agar) were performed on samples of blood and/or spleen and liver obtained from pigs that died or were killed by lethal injection.

Results. Results of *E. rhusiopathiae* challenge of control pigs are summarized in Table 2. All 10 pigs were positive for Erysipelas.

TABLE 2

Control pigs (T01) challenged with *E. rhusiopathiae*

| Pig number | Rectal temperature (40.9° C.) | | Clinical signs** | Treated (T), died (D), or humanely killed (K) | *E. rhusiopathiae* isolation results |
|---|---|---|---|---|---|
| | 2 days* | 1 day only | | | |
| 3017 | — | yes | yes | K | negative |
| 3022 | — | — | yes | D | positive |
| 3031 | yes | — | yes | T | no samples |
| 3046 | — | — | yes | K | negative |
| 3063 | — | yes | yes | K | positive |
| 3073 | yes | — | yes | T | no samples |
| 3085 | yes | — | — | T | no samples |
| 3090 | — | yes | yes | K | positive |
| 3103 | — | yes | yes | K | positive |
| 3110 | — | — | yes | D | positive |

*2 days - Elevation in rectal temperature above 40.9° C. on 2 consecutive days
**Clinical signs - Clinical signs included depression and/or metastatic skin lesions Results of the *E. rhusiopathiae* challenge of pigs given the vaccine with No.1 Adjuvant (T02) are summarized in Table 3. 15 of the 20 pigs (75%) were completely protected.

TABLE 3

Results of *E. rhusiopathiae* challenge of pigs given vaccine with No. 1 Adjuvant (T02)

| Pig number | Rectal temperature (40.3° C.) | | Clinical signs** | Treated (T), died (D), or humanely killed (K) | *E. rhusiopathiae* isolation results |
|---|---|---|---|---|---|
| | 2 days* | 1 day only | | | |
| 3006 | — | yes | — | — | no samples |
| 3010 | yes | — | yes | T | no samples |
| 3011 | — | yes | yes | T | no samples |
| 3025 | — | — | — | — | no samples |
| 3029 | — | yes | — | — | no samples |
| 3030 | — | — | — | — | no samples |
| 3033 | — | — | — | — | no samples |
| 3038 | — | — | — | — | no samples |
| 3047 | — | — | — | — | no samples |
| 3052 | — | — | — | — | no samples |
| 3059 | — | — | — | — | no samples |
| 3071 | — | — | — | — | no samples |
| 3088 | — | — | — | — | no samples |
| 3093 | — | — | — | — | no samples |
| 3098 | yes | — | yes | T | no samples |
| 3100 | — | — | — | — | no samples |
| 3112 | — | — | — | — | no samples |
| 3114 | yes | — | yes | T | no samples |

TABLE 3-continued

Results of *E. rhusiopathiae* challenge of pigs given vaccine with No. 1 Adjuvant (T02)

| Pig number | Rectal temperature (40.3° C.) | | Clinical signs** | Treated (T), died (D), or humanely killed (K) | *E. rhusiopathiae* isolation results |
|---|---|---|---|---|---|
| | 2 days* | 1 day only | | | |
| 3115 | — | yes | — | — | no samples |
| 3140 | — | yes | yes | D | positive |

*2 days - Elevation in rectal temperatures above 40.3° C. on 2 consecutive days
**Clinical signs - Clinical signs included depression and/or metastatic skin lesions Results of the *E. rhusiopathiae* challenge of pigs given the vaccine with saponin adjuvant (T03) are summarized in Table 4. Only one pig was protected.

TABLE 4

Results of *E. rhusiopathiae* challenge of pigs given vaccine with saponin adjuvant (T03)

| Pig number | Rectal temperature (40.3° C.) | | Clinical signs** | Treated (T), died (D), or humanely killed (K) | *E. rhusiopathiae* isolation results |
|---|---|---|---|---|---|
| | 2 days* | 1 day only | | | |
| 3014 | yes | — | yes | T | no samples |
| 3024 | — | yes | yes | T | no samples |
| 3034 | yes | — | yes | T | no samples |
| 3041 | yes | — | yes | T | no samples |
| 3048 | yes | — | yes | T | no samples |
| 3062 | — | yes | yes | T | no samples |
| 3075 | — | yes | — | — | no samples |
| 3095 | yes | — | yes | T | no samples |
| 3102 | — | yes | yes | T | no samples |
| 3106 | — | yes | yes | T | no samples |

*2 days - Elevation in rectal temperature above 40.3° C. on 2 consecutive days
**Clinical signs - Clinical signs included depression and/or metastatic skin lesions Geometric mean ELISA titers ("GMT"s) of piglet groups are listed in Table 5.

TABLE 5

Geometric mean ELISA titers of all treatment groups

| Treatment group* | Time (approximate) serum obtained | | | | | | |
|---|---|---|---|---|---|---|---|
| | Pre-vaccin. 1 | Pre-vaccin. 2 | 2 months | 3 months | 4 months | 5 months | Pre-challenge |
| 01 | 33.5 | 35.9 | 108.8 | 153.9 | 88.4 | 329.8 | 233.2 |
| 02 | 40.0 | 259.6 | 8903.9 | 1871.8 | 519.2 | 596.4 | 556.5 |
| 03 | 28.7 | 162.3 | 1712.9 | 527.2 | 199.8 | 302.8 | 459.0 |

*01 - placebo
02 - 3.2 opacity units of antigen in No. 1 Adjuvant
03 - 3.2 opacity units of antigen in saponin adjuvant Piglets had very low antibody titers specific for *E. rhusiopathiae* at the time of first vaccination. These titers ranged from less than 50 to 200. In control piglets, the GMT rose slightly during the course of the study indicating that the ELISA was less specific in older pigs.

The vaccines with either No.1 Adjuvant or saponin as adjuvant induced a statistically significant (P=0.0001) serological response that peaked at two weeks following second vaccination (approximately 2 months of age). Titers in both groups steadily declined over time (until approximately 5 months of age) with the GMT of piglets receiving antigen in No.1 Adjuvant being noticeably higher than the GMT of piglets receiving antigen in saponin adjuvant at all time points. At the time of challenge, the GMT of pigs receiving antigen in No.1 Adjuvant was slightly more than 2-fold higher than the GMT of the controls while the GMT of pigs receiving antigen in saponin adjuvant was slightly less than 2-fold higher than controls. Protection from clinical disease following challenge did not correlate with individual ELISA titer (P>0.05). However, an interesting observation was a peak titer observed two weeks after second vaccination in pigs given antigen in No.1 Adjuvant. Of the 20 piglets vaccinated with antigen in No.1 Adjuvant, eight had peak titers of greater than or equal to 2800 (8/8 protected from challenge), eight had peak titers of 6400 (6/8 protected from challenge), and 4 had peak titers of 3200 (¼ protected from challenge) suggesting that a titer that was 6400 or greater was an indicator of prolonged protection.

In summary, all 10 unvaccinated controls became infected. In the group of pigs given the vaccine with No. 1 Adjuvant, 15 of 20 were protected. In the group of pigs given the vaccine with saponin as adjuvant, only one of 10 was protected.

Example 4

Antigen Stabilization with Al Gel

A vaccine was prepared according to Examples 1–3, including treating the antigen with Al gel as described. The vaccine was tested for efficacy in pigs. Pigs were vaccinated with two 2 mL doses given intramuscularly (IM) one dose at about 3 weeks (weaning) and the second dose 3 weeks later. Controls received phosphate-buffered saline as a placebo. Immunity was challenged by the IM injection of virulent *E. Rhusiopathiae* at about 9 weeks of age. As shown in Table 6, protection due to vaccination was 100% at 9 weeks. This vaccine was already 12 months old at the time the pigs were vaccinated. The result confirms that the protective antigen was successfully stabilized.

TABLE 6

Protection of pigs against Erysipelas

| Age at Challenge | Controls (Protected/Challenged) | Vaccinates (Protected/Challenged) |
|---|---|---|
| 9 weeks | 0/10 | 19/19 |

Note: The 20th pig was excluded. A very fractious animal, it struggled so violently when handled that its temperature at rest could not be determined. Following challenge this pig remained completely healthy.

The invention is not to be limited in scope by the exemplified embodiments which are intended as illustrations of single aspects of the invention, and any antigens and vaccine compositions which are functionally equivalent are within the scope of the invention. Indeed, various modifications of the invention in addition to those described herein will become apparent to those skilled in the art from the foregoing description. Such modifications are intended to fall within the scope of the appended claims.

All publications cited herein are incorporated by reference in their entirety.

What is claimed is:

1. A vaccine composition comprising an antigen composition and an adjuvant composition, wherein the antigen composition comprises a fluid fraction of an *Erysipelothrix rhusiopathiae* culture and a stabilizing agent, wherein the *Erysipelothrix rhusiopathiae* culture is inactivated with beta-propiolactone or formalin and the stabilizing agent is aluminum hydroxide gel present at 30% v/v in said vaccine composition, and wherein the adjuvant composition comprises about 2% v/v lecithin, about 18% v/v mineral oil, and a combined volume of about 8% v/v of polyoxyethylene sorbitan monooleate and sorbitan monooleate surfactants with the remaining volume being a saline solution, wherein said vaccine composition is stable for at least one year and protects an animal against *Erysipelothrix rhusiopathiae* infection.

2. The vaccine composition of claim 1, wherein the animal is a pig or weaned pig.

3. The vaccine composition of claim 2, wherein the vaccine composition protects said weaned pig against *Erysipelothrix rhusiopathiae* infection for six months.

4. The vaccine composition of claim 1, wherein the fluid fraction of the antigen composition is concentrated 6 to 20 fold.

* * * * *